US006596740B2

(12) United States Patent
Jones

(10) Patent No.: US 6,596,740 B2
(45) Date of Patent: Jul. 22, 2003

(54) NICOTINE MUCOSAL SPRAY

(76) Inventor: Richard L. Jones, 10928-81 Street, Edmonton Alberta (CA), T5H 1L5

( * ) Notice: Subject to any disclaimer, the term of this patent is extended or adjusted under 35 U.S.C. 154(b) by 0 days.

(21) Appl. No.: 09/983,554

(22) Filed: Oct. 24, 2001

(65) Prior Publication Data

US 2002/0054856 A1 May 9, 2002

Related U.S. Application Data

(60) Provisional application No. 60/243,205, filed on Oct. 24, 2000.

(51) Int. Cl.$^7$ ............................ A61K 31/44; A61K 9/12
(52) U.S. Cl. ........................ 514/343; 424/1.13; 424/43; 424/434
(58) Field of Search ........................ 514/343; 424/1.13

(56) References Cited

U.S. PATENT DOCUMENTS

| | | | |
|---|---|---|---|
| 5,656,255 A | | 8/1997 | Jones |
| 5,721,257 A | | 2/1998 | Baker et al. |
| 5,780,051 A | * | 7/1998 | Eswara et al. ............... 424/423 |
| 6,277,855 B1 | * | 8/2001 | Yerxa ......................... 514/256 |

FOREIGN PATENT DOCUMENTS

| | | | |
|---|---|---|---|
| EP | 0619729 B1 | * | 7/1999 |

OTHER PUBLICATIONS

Tonnesen, P. et al., (1996) Recycling of hard–core smokers with nicotine nasal spray. Eur. Respir. J. 9: 1619–1623.
Benowitz, N. et al. (1998) Supression of Nicotine Intake During *Ad Libirum* Cigarette Smoking by High–Dose Transdermal Nicotine. The Journal of Pharmacology and Experimental Therapeutics 287(3): 958–962.
Herrera, N. et al., (1995) Nicotine Gum, 2 and 4 mg, for Nicotine Dependence. Chest 108(2): 447–451.
Leischow, S et al (1995) Nicotine polacrilex dose effects: serum nicotine levels and sensory characteristics. Psychopharmacology 117 125–129.
Blondal, T. et al. (1999) Nicotine nasal spray with nicotine patch for smoking cessation: randomised trial with six year follow up. BMJ 318: 285–289.
G. Sutherland et. al., (1992) Randomised controlled trial of nasal nicotine spray in smoking cessation. The Lancet 340: 324–329.
G. Sutherland et. al., (1994) Nasal nicotine spray for dependent smokers. J Smoking–Related Dis 5: 195–201.
A. Hjalmarson et. al., (1994) Effect of nicotine nasal spray on smoking cessation. Arch Int Med 154: 2567–2572.
N. G. Schneider et. al., (1995) Efficacy of nicotine nasal spray in smoking cessation: A placebo–controlled, double blind trial. Addiction 90: 1671–1682.
T. Blondal et. al., (1997) A double–blind randomized trial of nicotine nasal spray as an aid in smoking cessation. Eur Respir J 10: 1585–1590.

R. D. Hurt et. al., (1998) Nicotine nasal spray for smoking cessation: Pattern of use, side effects, relief of withdrawal symptoms and cotinine levels. Mayo Clin Proc 73: 118–125.
J. A. Stapleton et. al., (1998) How much does relapse after one year erode effectiveness of smoking cessation treatments? Long term follow up of randomised trial of nicotine nasal spray. Brit Med 316: 830–831.
R. L. Jones et. al., (1998) Nicotine and cotinine replacement when nicotine nasal spray is used to quit smoking. Psychopharmacology 137: 345–350.
M.A. H. Russell (1998) Nicotine replacement. The role of blood nicotine levels, their rate of change and nicotine tolerance. Alan R. Liss, Inc., New York.—Nicotine Replacement—a Critical Evaluation. In: Pomerleau OF, Pomerleau CS (eds), pp. 63–94.
K. O. Fagerstrom et. al., (1993) Effectiveness of nicotine patch and nicotine gum as individual versus combined treatments for tobacco withdrawal symptoms. Psychopharmacology 111: 271–277.
K. O. Fagerstrom (1978) Measuring degree of physical dependence to tobacco smoking with reference to individualization of treatment. Addictive Behaviours 3: 235:241.
K. J. Schuh et al., (1997) Nicotine nasal spray and vapor inhaler: abuse liability assessment. Psychopharmacology 130: 352–361.
K. A. Perkins et. al., (1994) Nicotine discrimination in male and female smokers. Psychopharmacology 116: 407–413.
K. A. Perkins et. al., (1994) Chronic and acute tolerance to subjective, behavioral and cardiovascular effects of nicotine in humans. Pharmacol Exp Ther 270: 628–638.
K. A. Perkins et. al., (1994) Comparison of acute subjective and heart rate effects on nicotine intake via tabacco smoking versus nasal spray. Pharmacol Biochem Behav 47: 295–299.
K. A. Perkins et. al., (1997) Acute reinforcing effects of low–dose nicotine nasal spray in humans. Pharmacol Biochem Behav 56: 235–241.
K. A. Perkins et. al., (1997) Nicotine discrimination and self–administration in humans as a function of smoking status. Psychopharmacology 131: 361–370.
C. D. Yu et. al., (1984) Cascade impactor method for the droplet size characterization of a metered–dose nasal spray. J Pharm Sci 73:344–348.
C. Feyerabend et. al., (1990) A rapid gas–liquid chromatographic method for the determination of cotinine and nicotine in biological fluids. J Pharm Pharmacol 42: 450–452.

* cited by examiner

*Primary Examiner*—William A. Jarvis
*Assistant Examiner*—Vickie Kim
(74) *Attorney, Agent, or Firm*—Bereskin & Parr; Anita Nador

(57) ABSTRACT

A composition for administration to the nasal mucosa of a subject comprises a solution of nicotine or a pharmaceutically acceptable salt thereof in a pharmaceutically acceptable solvent. The composition has a nicotine concentration less than 10 mg/ml. The composition used alone assists in reduction of the desire of a subject to smoke tobacco. It also reduces the nasal symptoms associated with administration of higher concentrations of nicotine to the nasal mucosa.

14 Claims, 5 Drawing Sheets

EFFICIENCY OF NICOTINE DELIVERY PER SPRAY

NICOTINE MUCOSAL SPRAY

RELATED APPLICATION

This application claims priority from U.S. Provisional Patent Application No. 60/243,205, filed Oct. 24, 2000, the entirety of which is herein incorporated by reference.

FIELD OF THE INVENTION

The invention relates to the field of nicotine mucosal sprays, to compositions comprising nicotine that can be administered in a mucosal spray form and to methods and uses therefore. In one embodiment, the invention relates to compositions and methods useful for subjects who wish to reduce tobacco smoking.

BACKGROUND OF THE INVENTION

Due to the reported harmful effects of tobacco smoke and also due to the current social attitudes to smoking, resulting in ever-increasing smoke-free public areas, there is great pressure on tobacco smokers to stop smoking or to find a more socially acceptable alternative. To achieve these goals various forms of nicotine-replacement therapy have been suggested. One such therapy is a nicotine nasal spray (NNS).

A commercially available NNS has a nicotine (concentration of 10 mg/ml (Nicotrol NS®, Pharmacia & Upjohn) and is described in U.S. Pat. No. 5,656,255 (the '255 patent). The '255 patent teaches a NNS with a lower limit of nicotine concentration of 10 mg/ml and a preferred concentration of 20 mg/ml (1). Studies using the 10 mg/ml product show that it is an effective aid to quitting smoking (2-9), especially for heavy smokers (2). Recent studies show that, in heavy smokers who successfully quit smoking while using 10 mg/ml NNS, venous plasma nicotine levels were approximately two-thirds the level seen while smoking (9). Therefore, 10 mg/ml NNS is an effective nicotine replacement therapy in which plasma nicotine levels reach the range where most of the nicotine withdrawal symptoms are avoided (10, 11). Studies leading to the '255 patent suggested that a nicotine concentration of 10 mg/ml was the lower limit capable of delivering sufficient nicotine to the blood plasma ($\frac{2}{3}$ of nicotine level seen while smoking) to avoid withdrawal symptoms.

Despite its demonstrated usefulness as a stop smoking aid, 10 mg/ml NNS causes many undesirable symptoms, the most common and severe of which are rhinorrhea (runny nose) and sneezing (2). Although these symptoms tend to moderate with continued use of 10 mg/ml NNS, many smokers stop using 10 mg/ml NNS because of the symptoms and, consequently, fail in their efforts to quit smoking (9).

Sutherland et al (2) have shown that heavy smokers (defined as those who score between 7 and 11 on the Fagerstrom Nicotine Tolerance Scale (12)) were more likely to quit smoking when using 10 mg/ml NNS than were lighter smokers who had lower plasma nicotine levels during unrestricted smoking. The lighter smokers (defined as those who score less than 7 on the Fagerstrom Scale) were as likely to quit smoking with placebo nasal spray as they were with 10 mg/ml NNS.

Although Schuh et al (13) assessed different doses of NNS they varied the dose by varying the number of sprays of 10 mg/ml NNS and not by varying the nicotine concentration in the spray. Unpublished observations from the inventors and observations published by Schuh et al (13) suggest that nasal symptoms are relatively independent of the number of sprays into the lose (one 0.05 ml spray of 10 mg/ml delivering 0.5 mg produces a response similar to two sprays of 10 mg/ml delivering 1 mg nicotine).

Perkins and his group (14–18) have studied the effects of various doses of nicotine nasal spray on physiological and behavioral function. Perkins' nasal spray delivery procedure is self-described as a method for research purposes (17) and not as a method suitable for clinical nasal spray trials, such as that conducted by Sutherland et al (2) and by the present inventors (9). Flerkins' technique involves spraying eight times (four sprays into each nostril) over a 2 minute period (18). The total volume of the eight sprays is 1.4 ml (0.175 ml/spray) and this volume stays constant. Such high volumes could not be used in a commercial product since considerable skill and a laboratory environment are requited to deliver and retain 1.4 ml and not have it run out the nose or drip backwards into the nasal pharynx.

In U.S. Pat. No. 5,721,257, Baker et al (19) describe a combination nicotine replacement therapy consisting of a nicotine skin patch to provide a steady level of blood nicotine which is supplemented, as required, by a nicotine nasal spray (nicotine concentration between 1 and 10 mg/ml) to provide transient increases in blood nicotine level of about 5 ng/ml. U.S. Pat. No. 5,721,257 (the '257 patent) teaches that it is the combination of nicotine replacement therapies that is effective and not the nicotine nasal spray. One disadvantage of the '257 patent is that it requires two different therapies. Another is that it is addressed to a nasal aerosol that is inhaled into the bronchioles of the lungs.

Accordingly, there remains a need for a nicotine therapy for assisting persons in stopping smoking and in reducing their desire to smoke.

SUMMARY OF THE INVENTION

The present invention provides novel methods and compositions for nicotine therapy. In one embodiment, the invention provides a composition for nasal administration of nicotine to a subject effective in increasing the nicotine plasma concentration of the subject to a level effective to assist the subject in quitting smoking and that results in reduced nasal symptoms as compared with other nicotine nasal sprays. Preferably, the composition results in minimal, and more preferably no nasal symptoms.

In a preferred embodiment, the invention provides a nicotine spray composition for administration to the nasal mucosa of a subject comprising a solution of nicotine or a pharmaceutically acceptable s It thereof in a pharmaceutically acceptable solvent, the solution having a nicotine concentration less than 10 mg/ml, preferably 1 to less than 9 mg/ml, more preferably from a out mg/ml, more preferably form about 5 to about 9.9 mg/ml. In a preferred embodiment of the invention, the pharmaceutically acceptable solvent is phosphate buffered saline. In another embodiment the pH of the solution is between about 5.0 and 8.0, more preferably between about 6.0 to 7.5 and most preferably about 7.0. The term "about" as used herein refers to +/−10% of the pH value.

In another embodiment, the invention provides a method that enables a subject to stop smoking and decreases the desire of a subject to smoke, the method comprising administering to the subject one source of an effective amount of nicotine, the source being in the form of a nicotine nasal spray composition that can be administered to the nasal mucosa of the subject, the composition comprising droplets having a size of about 10 or more microns and a solution of nicotine or a pharmaceutically acceptable salt thereof in a pharmaceutically acceptable solvent, said solution having a nicotine concentration less than 9 mg/m. In a particular embodiment, the nicotine solution has a pH in the range of about 5.0 to 8.0, preferably between about 6.0 to 7.5 and most preferably about 7.0.

In another embodiment, the nicotine nasal spray composition of the invention can be used to reduce nasal symptoms associated with the administration of nicotine to the nasal mucosa, the method comprising administering the composition of the invention to the nasal mucosa of a subject. In a preferred embodiment the nicotine nasal spray is in the form of droplets having a size of about 10 or more microns and is a solution of nicotine or a pharmaceutically acceptable salt thereof in a pharmaceutically acceptable solvent, the solution having a nicotine concentration less than 10 mg/ml and, preferably, a nicotine concentration in the range of about 5 mg/ml to less than 10 mg/ml. The term "about" as used herein refers to +/−10% of the concentration value.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to tie drawings in which:

FIG. 5 is a bar graph showing the efficiency of nicotine uptake into the blood per spray.

DETAILED DESCRIPTION OF THE INVENTION

Definitions

Figure 1:
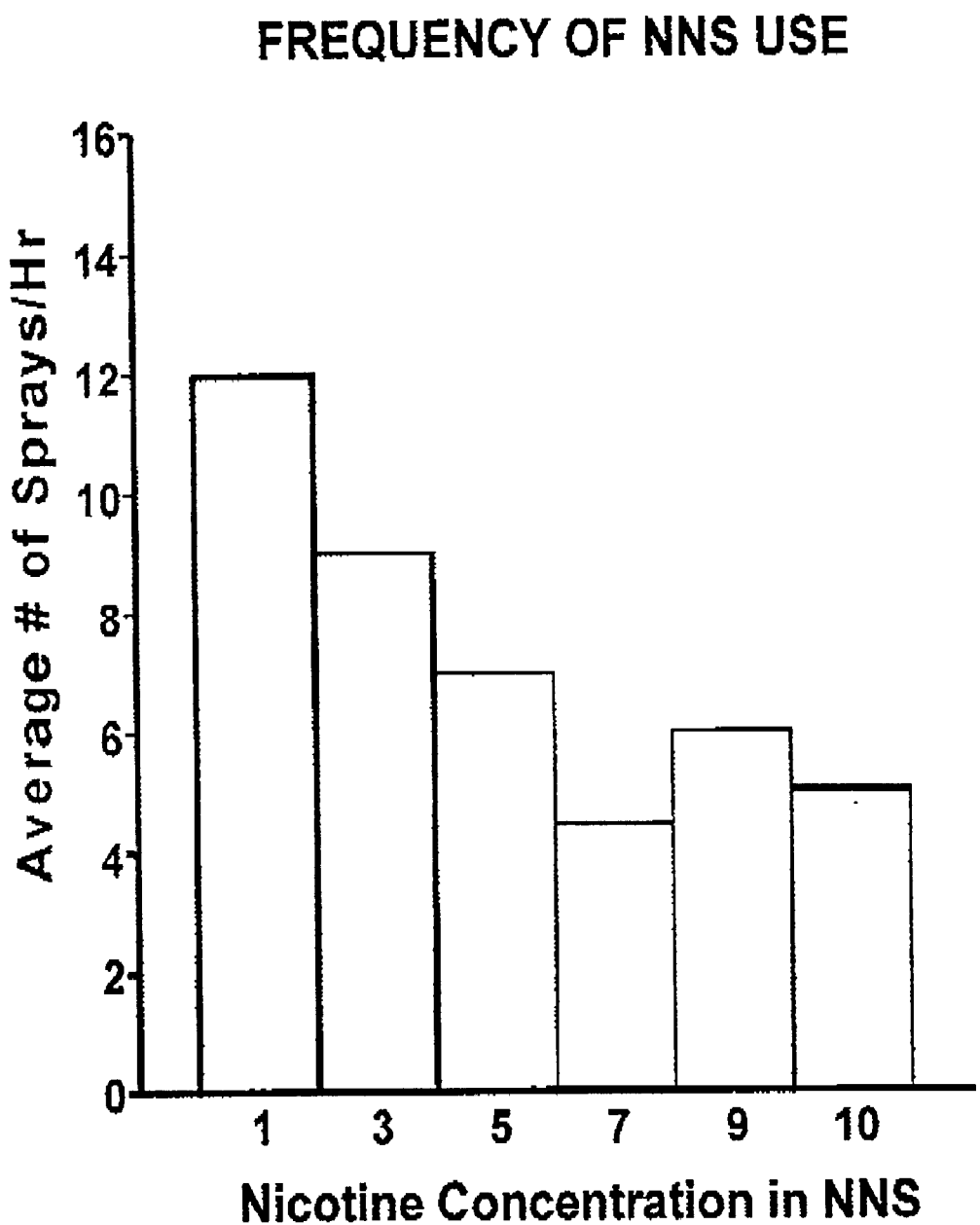
FIG. 1 is a bar graph of the frequency of NNS uses by a subject.

The term "effective amount" means an amount effective, at dosages and for periods of time necessary to achieve the desired result A person skilled in the art would appreciate that the effective amount can vary depending on the age, sex, and weight of the subject. In the present invention when referring to an effective amount of nicotine for assisting a subject to stop smoking, the effective amount may vary depending on the degree the subject smoked (i.e. number of cigarettes per day).

The term "subject" means a human subject.

The term "increasing plasma nicotine concentration" is defined as increasing the plasma nicotine concentration above the baseline plasma nicotine concentration. The increase in plasma nicotine concentration can be assessed by methods well known in the art including the method described by Fayerabend and Russell and used herein (21).

The term "nasal symptoms" means the undesirable physiological symptoms caused by administering nicotine to the nasal mucosa of a subject, primarily rhinorrhea, sneezing, throat irritation, watery eyes and other less frequent symptoms (2).

The term "reducing nasal symptoms" means reducing the severity of one or more nasal symptoms experienced by a subject using a nicotine spray with a nicotine concentration of 10 mg/ml or more.

The term "reducing the desire to smoke tobacco" means providing a subject with an effective way of obtaining nicotine without resorting to smoking tobacco. A commonly used method for assessing the craving for nicotine can be found in the Diagnostic and Statistical Manual of Mental Disorders (DSM-III-R) (see (1991) J. Am. Med. Assoc. 266:3133) This source uses a 4-point scale to rate nicotine craving from none (rating 0) to severe (rating 4). An effective nicotine replacement should result in at lease a 1-point decrease in the nicotine craving score.

The term "pharmaceutically acceptable salt" means an acid salt or a basic salt which is suitable for or compatible with the treatment of a subject. Pharmaceutically acceptable salts of nicotine are known to those skilled in the art and include nicotine tartrate and nicotine hydrogen tartrate The term "pharmaceutically acceptable solvent" means a solvent that is physiologically tolerable at the dosage administered. Nicotine is soluble in water but an aqueous solvent should have it's pH adjusted with buffers and it's osmolarity adjusted into the physiological range. Those skilled in the art will know how to accomplish these adjustments.

The term "one source" when referring to "one source of nicotine" as used herein means a single form of nicotine other than, or in addition to tobacco smoke and does not include multiple alternative sources for nicotine, for example, the use of a nicotine patch, a nicotine nasal spray, nicotine lozenges or other form. However in the context of the application, it should be understood that a subject may, at least on occasion, be smoking tobacco in addition to administering the one source of nicotine in accordance with the methods and uses of the present invention.

DETAILED DESCRIPTION

The present invention provides a convenient, inexpensive and effective way to increase the nicotine plasma levels in a subject by administration of an effective amount of nicotine by nasal spray to a subject. In a preferred embodiment the present invention assists subjects in quitting tobacco smoking. In another embodiment, the invention provides a convenient, inexpensive, and effective way to increase nicotine plasma levels in a subject as an alternative to tobacco smoking by administering a nicotine nasal spray composition to a subject.

Nicotine-containing compositions and nasal strays suitable for nasal administration, and delivery of the nicotine to the nasal mucosa of a subject are also provided. Preferably, the nicotine compositions are suitable to be formed into a nasal spray composition and administered by nasal spray. "Suitable for nasal administration and delivery" as used herein refers to any form of the nasal spray composition that can be delivered so. A person skilled in the art would be familiar with suitable preparation forms. Preferably, the nicotine nasal spray composition suitable for nasal administration is in a form and is delivered by a nebulizer or atomizer that generates droplet sizes of about 10 or greater microns, more preferably about 10–200 microns, most preferably about 10–100 microns.

The smoking alternative provided by the present invention may be used to assist those attempting to stop tobacco smoking or may be used indefinitely as circumstances dictate as a substitute for tobacco smoking which avoids both the undesired side effects of tobacco smoking on other people in the vicinity of the smoker and also the deleterious effects on the smoker of other substances such as carcinogens and carbon monoxide in tobacco smoke. When the nicotine-containing solution is applied to the nasal mucosa, nicotine can be absorbed directly into the bloodstream if a smoking substitute is to be provided by this means, sufficient nicotine must be applied and absorbed to give a rapid increase in blood nicotine comparable to that achieved by tobacco smoking if the craving to smoke is to be eliminated, either in the short term as a tobacco substitute or in the long term as a smoking cessation aid. Previously available smoking substitutes often fail in this regard due to a too small or too delayed increase in blood nicotine levels.

It is desirable that nasal administration of nicotine provides a sufficient dose of nicotine to a sufficiently large area of the nasal mucosa to give the desired rapid increase in blood nicotine level without providing a local nicotine concentration so high that it causes mucosal irritation and without requiring the delivery of such a large volume of nicotine-containing composition that a portion of the administered dose runs from the nose, causing annoyance and inconvenience to the user.

In accordance with the present invention, nicotine or a pharmaceutically acceptable nicotine salt is dissolved in a pharmaceutically acceptable solvent, such as phosphate-buffered saline, and is adjusted to pH in the range of about 5.0 to 8.0, preferably 6.0–7.5 and most preferably to a pH of about 7.0.

In accordance with a preferred embodiment of the invention, a composition having a nicotine concentration of less than 10 mg/ml, dissolved in phosphate buffered saline at a pH of about 7.0 is employed. The composition is delivered to the nose by a spray device which preferably delivers about 0.05 ml of the composition per activation of a suitable pump-type nasal spray atomizer in the form of a spray having droplets of about 10 microns or more in diameter.

The nicotine composition of the invention may also optionally contain one or more of a flavouring agent such as menthol, and preserving agent such as benzoic acid or an antioxidant such as ascorbic acid Suitable flavourings and preservatives acceptable in foods and pharmaceuticals will be known to those skilled in the art, as well as suitable concentrations of these agents.

The nicotine-containing composition of the present invention is applied to the nose as a spray of droplet size selected to favour deposition of the droplets in the nose and minimise inhalation of the nicotine composition into the airways beyond the nose where irritation of the upper respiratory tract can result in immediate and severe symptoms.

Studies by Yu et al (20) have shown that droplet size of a spray delivered into the nose or inhaled through the mouth influences the location of droplet deposition These authors showed that, during inhalation, droplets of 2 to 6 microns largely reach the terminal bronchi and alveoli, whereas a majority of droplets greater than 10 microns is required to localise delivery to the nasal mucosa.

The nicotine-containing composition of the invention may be applied to the nose by any suitable atomiser or spray device which produces a spray of droplet size greater than about 10 microns. For example, conventional venturi-type atomisers such as are used for nasal decongestants or metered dose spray devices may be employed. These devices produce 98% of droplets greater than 16 microns and a majority of droplets are approximately 100 to 200 microns.

When the nasal spray of the invention is used, nicotine is not drawn into the user's airways beyond the nose, thus avoiding respiratory irritation and allowing the use of higher nicotine concentrations, permitting bloods nicotine levels to be boosted into the range which reduces nicotine withdrawal symptoms without concomitant irritation.

Lower concentrations of nicotine cause less rhinorrhea thus permitting the dose, although it is smaller than that from 10 mg/ml, longer access to the nasal mucosa with more efficient nicotine uptake into the blood. Using an NNS with nicotine concentrations less than 10 mg/ml, preferably 1 to less than 10 mg/ml, more preferably from about 5 to about 9 mg/ml, results in plasma nicotine levels similar to those observed from use of 10 mg/ml NNS (see Example 1) Use of an NNS with nicotine concentrations less than 10 mg/ml, preferably 1 to less than 10 mg/ml, more preferably from about 5 to about 9 mg/ml can, therefore, be an effective way of treating a disorder such as addiction to nicotine from cigarette smoking or of decreasing a subject's desire to smoke cigarettes. It will be appreciated that a NNS having a nicotine concentration of 1 mg/ml could be effective, but is not preferred where a subject is trying to stop smoking or decrease a desire to smoke, as the spray volume required to generate a suitable plasma nicotine level would not be convenient, and would be impractical and socially undesirable. Thus a suitable concentration of nicotine solution should be selected that is both convenient and socially desirable.

The inventors have found that in a preferred embodiment, the composition of the invention can be applied in a volume of about 0.05 ml to 0.10 ml per nostril with good retention of the composition in the nose. A nicotine concentration of less than 10 mg/ml, preferably 1 to less than 10 mg/ml, more preferably from about 5 to about 9 mg/ml is well tolerated by the nasal mucosa and reduces the nasal symptoms, primarily rhinorrhea and sneezing, observed when using solutions of higher nicotine concentration In order to approximate the dose of nicotine delivered to the blood by smoking one cigarette, (approximately 1 mg (Russell et al. (10)) about 2 mg nicotine should be delivered to the nose. If, for example, an atomiser delivering about 0.03 ml. nicotine composition per squeeze is employed, and the composition has a concentration of 20 mg/ml nicotine, one squeeze delivers 0.06 mg nicotine and three applications will deliver approximately 2 mg nicotine.

A method of increasing the plasma nicotine concentration of a subject involves administering to the nasal mucosa of a subject, a nicotine spray with a nicotine concentration of less than 10 mg/ml, preferably 1 to less than 10 mg/ml, more preferably from about 5 to about 9 mg/ml and with a pH in the range of 5.0 to 8.0, preferably 6.0 to 7.5 and most preferably about 7.0. Preferably, the nicotine spray is the sole source of nicotine for the subject.

A method of reducing nasal symptoms, primarily rhinorrhea and sneezing associated with using a nicotine spray with concentration is of nicotine of 10 mg/ml or greater involves administering as a sole source of nicotine, nicotine spray with a nicotine concentration of less than 10 mg/ml, preferably 1 to less than 10 mg/ml, more preferably from about 5 to about 9 mg/ml and with a pH in the range of 5.0 to 8.0, preferably 7.0, to the nasal mucosa of a subject. The inventors have unexpectedly found that administering a nicotine spray in accordance with this preferred embodiment results in similar blood plasma nicotine levels as from a nicotine spray with a nicotine concentration of 10 mg/ml.

A method of reducing the desire of a subject to, smoke tobacco or of providing a smoker with a substitute for smoking tobacco involves administering to the nasal mucosa of a subject, once source of an effective amount of nicotine in the form of a nicotine spray with a nicotine concentration of less than 10 mg/ml, preferably 1 to less than 10 mg/ml, more preferably from about 5 to about 9 mg/ml and with a pH in the range of 5.0 to 8.0, preferably 6.0 to 7.5 and most preferably about 7.0.

The methods can be effective in treating heavy smokers, those who consume more than one package of about 20 cigarettes per day (Fagerstrom score of 7 or more), or light smokers, those who smoke less than 1 package of about 20 cigarettes per day (Fagerstrom score of less than 7). The inventors have found that a nicotine nasal spray with a nicotine concentration of 10 mg/ml or more, does not benefit light smokers as much as it does heavy smokers is light smokers are not as inclined to suffer through the nasal symptoms caused by the nicotine and are likely to quit using the nasal spray before quitting smoking entirely. Heavy smokers seem more inclined to suffer through the nasal symptoms and may benefit more from a spray with a concentration of 10 mg/ml or more. However, a nicotine nasal spray in accordance with the preferred embodiments will be of benefit to both heavy smokers and light smokers since the resultant blood nicotine level is similar to that obtained from a NNS of 10 mg/ml yet the nasal irritation is less.

Other uses of the composition of the invention may be evident to those skilled in the art upon reading the present description. For instance, the compositions of the invention can be used where increasing the plasma nicotine levels is indicated or desired, such as in various neurological diseases such as Parkinson's and Alzheimer's, and can be used to relieve a smoker's desire for nicotine in environments where smoking is prohibited, such as in commercial aircraft.

The following non-limiting example is illustrative of the present invention.

EXAMPLES

Example 1

A 54 year old male with a 30 pack-year history of cigarette smoking is used here to illustrate the effectiveness of NNS's with nicotine concentrations less than 10 mg/ml. He successfully quit smoking in 1996 with the aid of 10 mg/ml NNS. He continued to use NNS daily from 1996 until this study in 1998. He had normal lung and cardiovascular function. His aerobic capacity at maximal exercise was 140% of the predicted capacity for his age and size.

Five concentrations of NNS where prepared from base solution containing 10 mg/ml nicotine. The (−) isomer of nicotine (the naturally occurring form) was obtained from Sigma-Aldrich Canada Ltd (Oakville, ON, Cat# N3876). To make the 10 mg/ml nicotine solution, 1 gm of nicotine was dissolved in 100 ml phosphate-buffered saline. Phosphate-buffed saline (PBS) was prepared by adding 0.71 gm $Na_2HPO_4$ and 0.69 gm $Na_2HPO_4$ to sterile distilled $H_2O$ to make 100 ml. Then 0.92 gm NaCl was added. The resulting solution had a pH of 6.8 and an osmolarity of 290 mOsm. The five lower nicotine concentrations contained 9, 7, 5, 3 and 1 mg/ml of nicotine. The 9 mg/ml solution was prepared by diluting 18 ml of the base solution (10 mg/ml) with 2 ml PBS. The 7 mg/ml solution contained 14 ml of the base solution and 6 ml of PBS, the 5 mg/ml solution contained 14 ml of the base solution and 14 ml PBS, the 3 mg/ml solution contained 6 ml of the base solution and 14 ml PBS and the 1 mg/ml solution contained 2 ml of the base and 18 ml PBS. The viscosity of the solutions was near 1.0 cps (similar to water).

Since the technician who prepared the nicotine-containing solutions was also the person who analyzed the blood plasma for its nicotine concentration, another person randomly labelled each concentration with a letter from A–F and he kept the concentration-letter code confidential. The subject then randomly used sprays A–F but the venous blood samples were labelled only according to date and time Therefore, both the technician who prepared the NNS solutions and analyzed the plasma nicotine and the subject who used the NNS were blinded as to which concentration was being used on a given day. The actual order of use was B, D, E, A, C and F. When the blinding code was broken, the order of administration was discovered to be: 1, 10, 3, 9, 5, and 7 mg/ml.

The subject did not use NNS or other sources of nicotine for ten hours prior to having a baseline venous blood sample taken at 08:00. All blood samples were collected in heparinized Vacutainers®, immediately centrifuged in a Beckman TJ-6 centrifuge at 3000 rpm for 15 minutes and then frozen at −70° C. until plasma nicotine concentration was measured.

The plasma nicotine was measured in duplicate bee the method of Fayerabend and Russell (20). Venous blood samples were taken again at four and at six hours after commencing NNS use and at least 15 min after the subject had taken a dose of NNS.

The various concentrations were placed in labelled metered nasal spray pump atomizers which delivered 0.05 ml/squeeze. The subject was permitted unrestricted use of the NNS and, with a pencil taped to the NNS pumps he marked the time of each spray The studies were done during normal office working hours with the subject being a university professor without teaching commitments at the time of the study. A separate NNS concentration was used on successive days from Tuesday to Thursday during two consecutive weeks. The plasma nicotine levels reported are the average of the four and six hour blood samples when a steady state of plasma nicotine is achieved. Unpublished observations from the inventor indicate that steady state blood nicotine levels are achieved within four hours of ad libitum NNS use.

Blood levels of nicotine resulting from unrestricted, but blinded, use of 10 mg/ml NNS were compared with those resulting from use of NNS's with concentrations less than 10 mg/ml (1, 3, 5, 7, and 9 mg/ml).

FIG. 1 shows the frequency of using the different NNS solutions, measured in number of sprays. There was a tendency for NNS use to decrease as nicotine concentration increased but there was very little differed ice in the frequency of using the 7, 9 and 10 mg/ml solutions.

Figure 2:
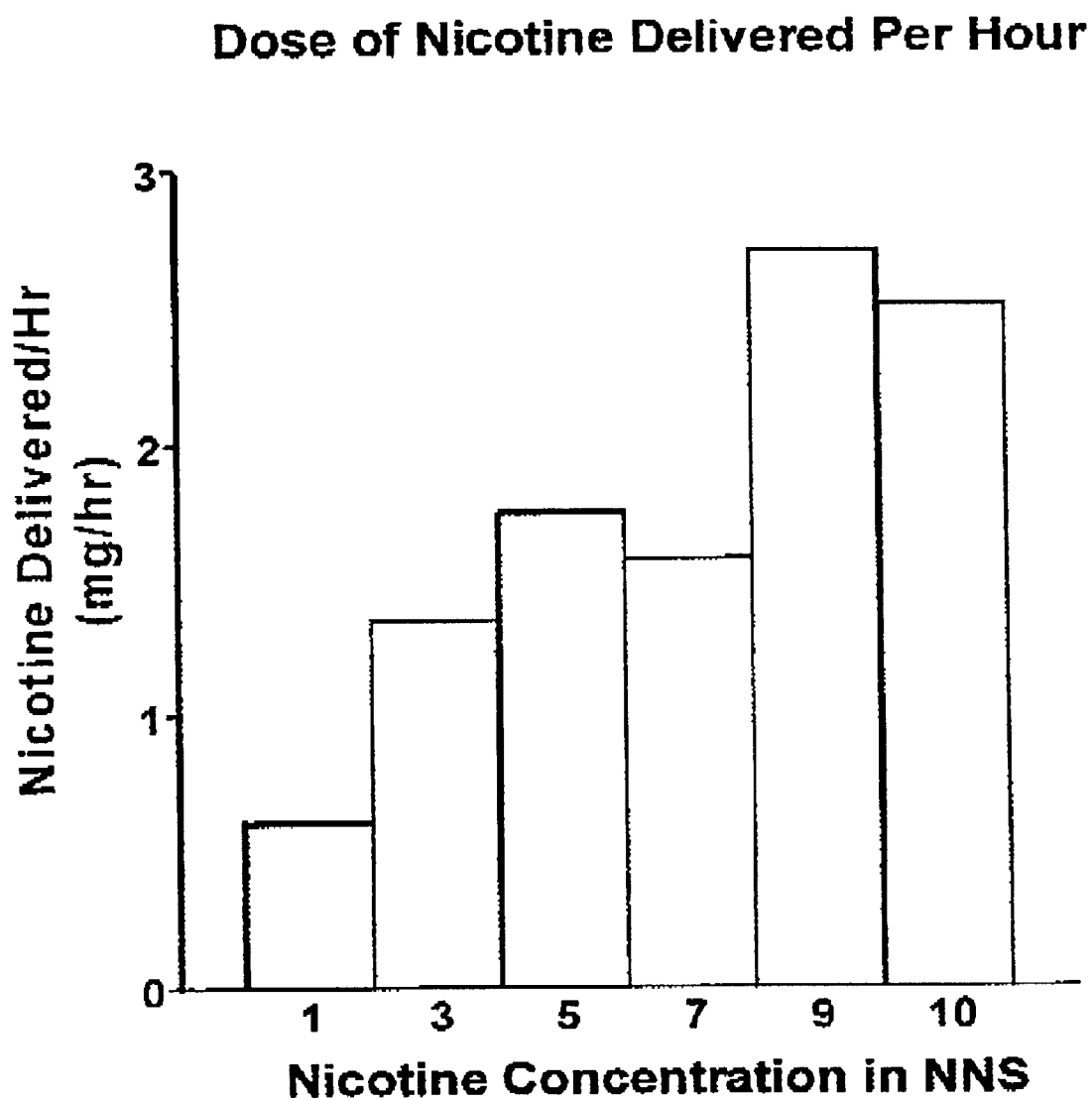
FIG. 2 is a bar graph showing the dose of nicotine delivered to the nasal mucosa per hour by a subject.

FIG. 2 shows the amount (mg/hr) of nicotine delivered, which is dependent on both the spraying frequency and on the nicotine concentration of the spray. FIG. 2 shows a tendency for the delivered dose to increase with NNS solutions having the higher nicotine concentrations despite the lower spraying frequency (FIG. 1).

Figure 3:
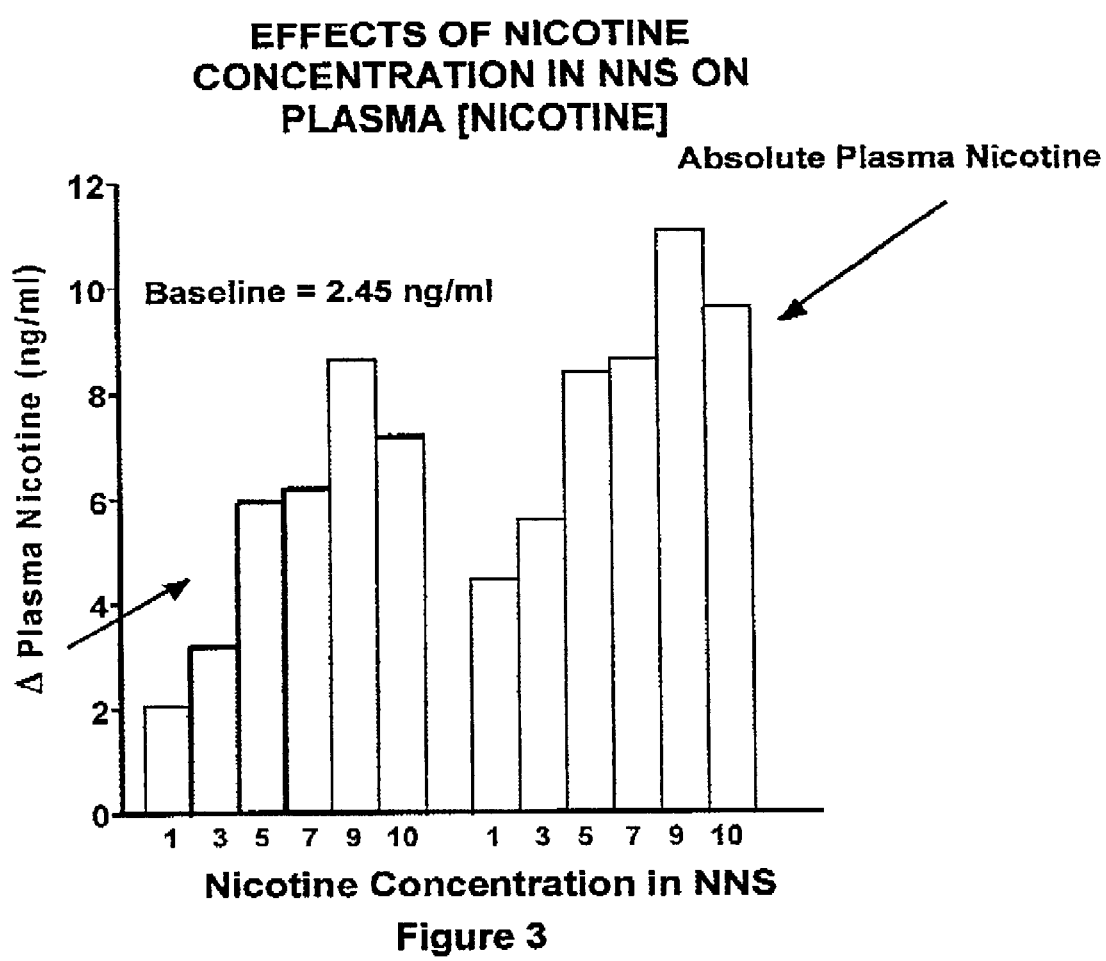
FIG. 3 is a bar graph showing the effect of the variation in nicotine concentration in NNS on plasma nicotine levels in a subject.

FIG. 3 shows the plasma nicotine concentrations resulting from the use of NNS's with different concentrations, reported as the absolute values and as the change from the baseline plasma nicotine concentration, which averaged 2.45 mg/ml after 10 hours of not using NNS. As larger doses of nicotine were delivered to the nasal mucosa with the use of the higher nicotine concentrations, higher plasma levels of nicotine were expected and observed when the subject used the higher nicotine concentrations. The plasma nicotine levels observed in FIG. 3 resemble the pattern seen for the dose delivered (FIG. 2). All six NNS solutions increased plasma nicotine but there was very little difference between nicotine sprays containing 5, 7, 9, and 10 mg/ml.

Figure 4:
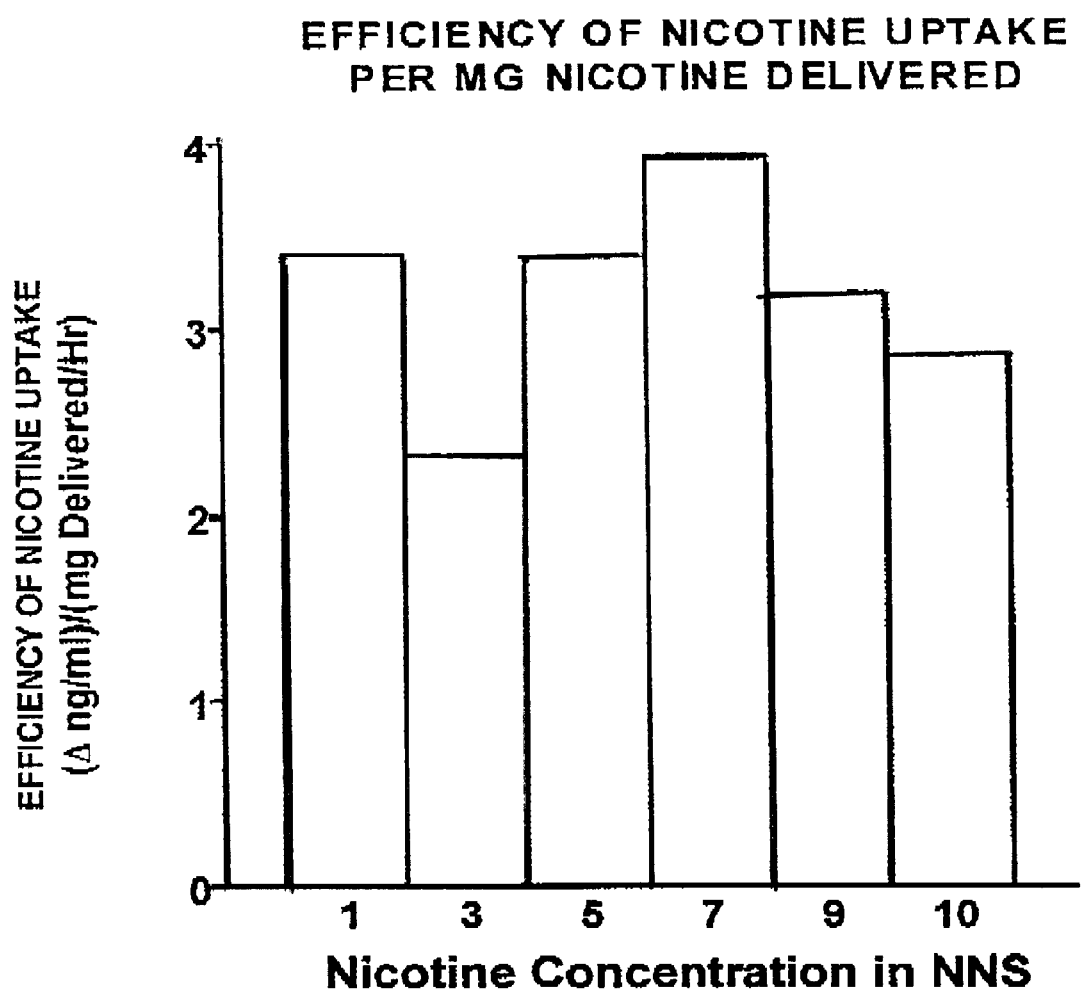
FIG. 4 is a bar graph showing the efficiency of nicotine uptake into the blood per mg of nicotine delivered to a subject.

The effectiveness of nicotine uptake was calculated in two different ways. The first method involved dividing the change in venous plasma nicotine concentration (FIG. 3) by the dose delivered to the nose between four and six hours of NNS use (FIG. 2). The results of this calculation are illustrated in FIG. 4, and are expressed in units of (ng/ml)/(mg delivered/hour). The mg delivered were determined by multiplying the volume of each spray (0.05 ml) by the average number of spray activations per hour and also by the nicotine concentration in the solution. As FIG. 4 illustrates, the efficiency of nicotine uptake from the 1, 5, 7 and 9 mg/ml solutions was at least as high as that for the 10 mg/ml solution. This indicates that nicotine from NNS solutions having less than 10 mg/ml can be taken up as well as, or better than, nicotine from a 10 mg/ml NNS.

Figure 5:
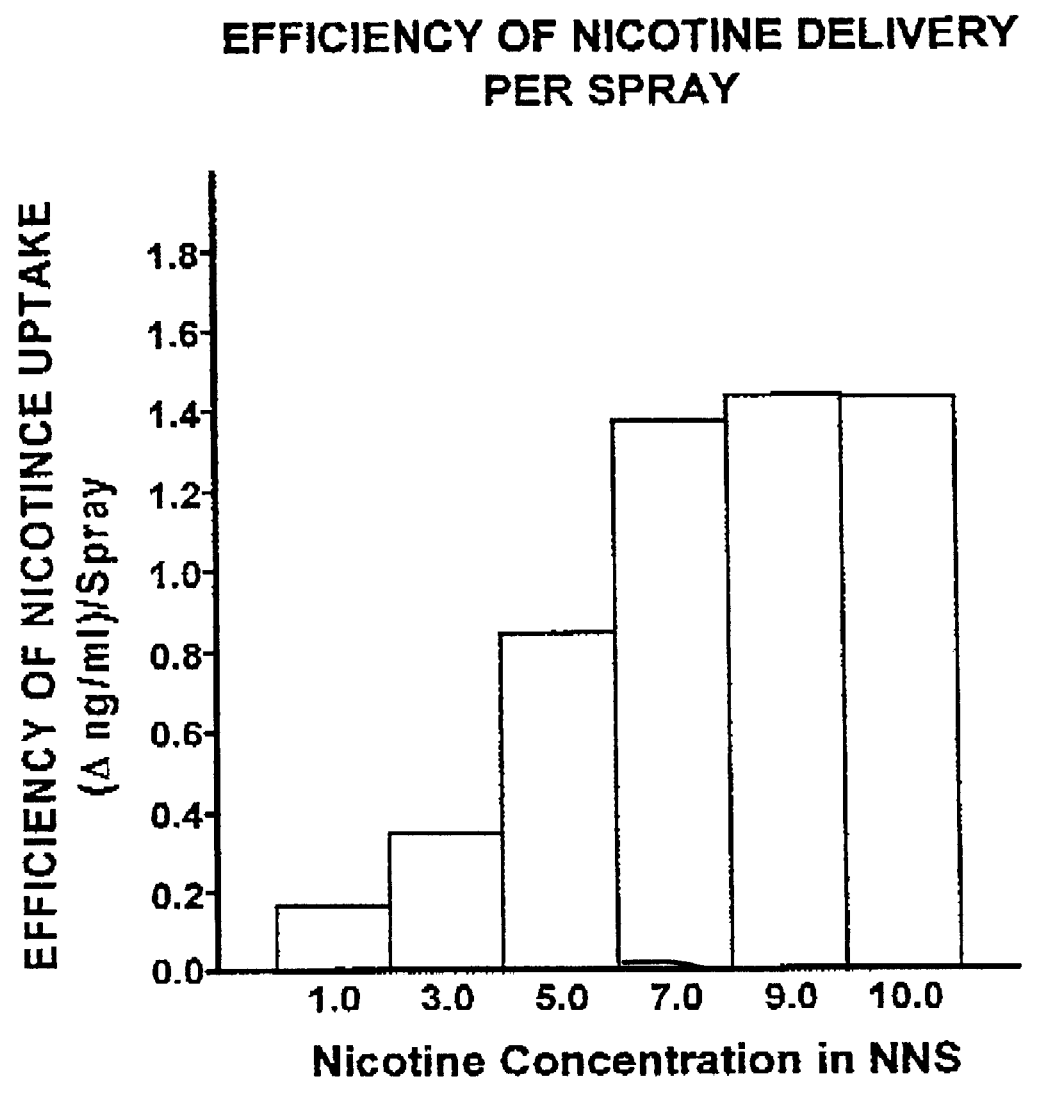

The second method of determining effectiveness involved dividing the change from baseline plasma nicotine level (FIG. 3) by the average spray activations per hour between four and six hours of NNS use (FIG. 1). The results of this calculation are in units of (ng/ml)/(sprays/hour) and are shown in FIG. 5. The calculation omits the delivered nicotine dose but it does give insight into the efficiency of achieving a plasma nicotine level by adjusting the spraying frequency. There was no difference between 7, 9 and 10 mg/ml solutions. This indicates that, despite the different concentrations in these three sprays, there is an equal nicotine uptake for each spray activation. The lower values observed for the 1, 3 and 5 mg/ml concentrations is expected since more sprays of these solutions were required to achieve the final plasma nicotine concentration.

These results indicate that use of an NNS with nicotine concentrations less than 10 mg/ml adds significant nicotine to the blood. In particular, nicotine concentrations of 5, 7, and 9 mg/ml resulted in similar plasma nicotine concentrations to those observed from the use of the 10 mg/ml solution. Theoretically, these lower concentrations should also function well as smoking cessation aids for all smokers, including heavy smokers. However, it is possible that NNS solutions with less than 5 mg/ml could also be effective since they also increase plasma nicotine concentration.

FIG. 5 indicates that the plasma nicotine concentration resulting from each spray is similar for the 7, 9, and 10 mg/ml solutions this is consistent with low nicotine concentrations being taken up more efficiently than 10 mg/ml. It is possible that a dilution effect occurs when using a 10 mg/ml solution delivered to the nasal mucosa due to greater rhinorrhea and some of the 10 mg/ml solution may be lost from the nasal mucosa when the nose is blown in response to the rhinorrhea.

Although 1, 3, and 5 mg/ml NNS solutions resulted in lower plasma nicotine concentration per spray activation (FIG. 5) the similar plasma nicotine per dose delivered for all of the concentrations tested (FIG. 4) indicates that increasing spraying frequency of 1, 3, and 5 mg/ml solutions could result in higher plasma nicotine levels, similar to those obtained by 7, 9 and 10 mg/ml.

That the change in plasma nicotine per spray activation was similar for 7, 9 and 10 mg/ml (FIG. 5) is important as it indicates that the same concentration of plasma nicotine can be achieved with less nicotine being delivered to the nasal mucosa, which should lower the incidence of nasal symptoms with use of the lower nicotine-containing nasal sprays.

NNS solutions containing 1, 3 and 5 mg/ml could be as effective as the 7, 9 and 10 mg/ml solutions if these lower concentrations were sprayed more frequently Increasing the spraying frequency is possible since the NNS solutions are delivered using a relatively low spray volume. However, fewer, rather than more, sprays per hour is preferable and for practical purposes, nicotine concentrations less than 10 mg/ml, preferably from about 5 mg/ml to less than 10 mg/ml provide better results.

The results indicate that nicotine nasal sprays having between 5 and 9 mg/ml nicotine can be as effective as the 10 mg/ml product as an alternative to smoking cigarettes and to help smokers quit smoking. They can be used as the sole source of nicotine in the methodologies of the present invention. Concentrations under 5 mg/ml could also be useful as nicotine replacement therapies and their usefulness would be dependent on the relatively low blood nicotine levels they produce.

Evidence of the effectiveness of NNS containing less than 10 mg/ml nicotine comes from other results of a smoking cessation study (data not included) utilizing the 10 mg/ml commercial product. Two subjects who successfully quit smoking for the three months of the study (9) and who used the NNS throughout the study, desperately wanted to remain non-smokers following the study when 10 mg/ml NNS was no longer available to them. They were given 8 ml/ml NNS, prepared as described above. They were also given nicotine-free normal saline and encouraged to dilute the 8 mg/ml NNS so as to function on the lowest possible nicotine intake. Both subjects reported that they could remain symptom-free using concentrations of 4 mg/ml, and sometimes lower. Although this could not be confirmed, the highest concentration they could have used was 8 mg/ml, which is in the range reported as effective in the study described above. Both subjects also reported fewer nasal symptoms when using the NNS solutions having nicotine concentrations less than 10 mg/ml compared to the 10 mg/ml solution used during the study.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

FULL CITATIONS FOR REFERENCES
REFERRED TO IN THE SPECIFICATION

1. Jones R. L.: Composition to help stop smoking. U.S. Pat. No. 5,656,255. Issue date Aug. 12, 1997, application date Sep. 29, 1994.
2. Sutherland G, Stapleton J A, Russell M A H, Jarvis M J, Hajek P, Belcher M, Feyerabend C (1992) Randomised controlled trial of nasal nicotine spray in smoking cessation. Lancet 340: 324–329.
3. Sutherland G, Stapleton J A (1994) Nasal nicotine spray for dependent smokers. J Smoking-Related Dis 5:195–201.

4. Hjalmarson A, Franzon M, Westin A, Wiklund O (1994) Effect of nicotine nasal spray on smoking cessation. Arch Int Med 154: 2567–2572.
5. Schneider N G, Olmstead R, Mody F V, Doan K, Franzon M, Jarvik M E, Steinberg C (1995) Efficacy of nicotine nasal spray in smoking cessation: A placebo-controlled, double blind trial. Addiction 19: 1671–1682.
6. Blondal T, Franzon M, Westin A (1997) A double-blind randomized trial of nicotine nasal spray as an aid in smoking cessation. Eur Respir J 10: 1585–1590.
7. Hurt R D, Dale L C, Croghan G A, Croghan I T, Gomez-Dahl L C, Offord K P (1998) Nicotine nasal spray for smoking cessation: Pattern of use, side effects, relief of withdrawal symptoms and cotinine levels. Mayo Clin Proc 73: 118–125.
8. Stapleton J A, Sutherland G, Russell M A H (1998) How much does relapse after one year erode effectiveness of smoking cessation treatments? Long term follow up of randomized trial of nicotine nasal spray. Brit Med J No.7134, 316:830–831.
9. Jones R L, Nguyen A, Man S F P (1998) Nicotine and cotinine replacement when nicotine nasal spray is used to quit smoking. Psychopharmacology 137: 345–350.
10. Russell M A H (1988) Nicotine replacement. The role of blood nicotine levels, their rate of change and nicotine tolerance. In: Pomerleau O F, Pomerleau C S (eds) Nicotine Replacement—a Critical Evaluation. Alan R, Liss, Inc., New York.
11. Fagerstrom K O, Schneider N G, Lunell E (1993) Effectiveness of nicotine patch and nicotine gum as individual versus combined treatments for Tabasco withdrawal symptoms. Psychopharmacology 111: 271–277.
12. Fagerstrom K O (1978) Measuring the degree of physical dependence to tobacco smoking with reference to individualization of treatment. Addictive Behaviours 3: 235–241.
13. Schuh K J, Schuh L M, Henningfield J E, Stitzer M L (1997) Nicotine nasal spray and vapor inhaler: Abuse liability assessment. Psychopharmacology 130: 352–361
14. Perkins K A, DiMarco A, Grobe J E, Scierka A, Stiller R L (1994) Nicotine discrimination in male and female smokers. Psychopharmacology 116: 407–413.
15. Perkins K A, Grobe J E, Fonte C, Goettler J, Caggiula A R, Reynolds W A, Stiller R L (1994) Chronic and acute tolerance to subjective behavioral and cardiovascular effects of nicotine in humans. Pharmacol Exp Ther 270: 628–638.
16. Perkins K A, Sexton J E, Reynolds W A, Grobe J E, Fonte C, Stiller R L (1994) Comparison of acute subjective and heart rate effects on nicotine intake via tobacco smoking versus nasal spray. Pharmacol Biochem Behav 47: 297–299.
17. Perkins K A, Grobe J E, Caggiula A, Wilson A S, Stiller R L (1997) Acute reinforcing effects of low-dose nicotine nasal spray in humans. Pharmacol Biochem Behav 56: 235–241.
18. Perkins K A, Sanders M, D'Amico D, Wilson A, (1997) Nicotine discrimination and self-administration in humans as a function of smoking status. Psychopharmacology 131: 361–370.
19. Baker R, Santus G, Vintilla-Friedman S.: Method and therapeutic system for smoking cessation. U.S. Pat. No. 5,721,257. Issue date Feb. 24, 1998, application date Jun. 7, 1995.
20. Yu C D, Jones R E, Henesian M (1984) Cascade impactor method for the droplet size characterization of a metered-dose nasal spray. J Pharm Sci 73: 344–348.
21. Feyerabend C, Russell M A H (1990) A rapid gas-liquid chromatographic method for the determination of cotinine and nicotine in biological fluids. J Pharm Pharmacol 42: 450–452.

What is claimed is:

1. A method for reducing nasal symptoms associated with the administration of nicotine to the nasal mucosa of a subject comprising administering to the subject one source of an effective amount of nicotine, said source being in the form of a nicotine nasal spray composition that can be administered to the nasal mucosa of the subject, the composition comprising droplets having a size of about 10 microns or more and a solution of nicotine or a pharmaceutically acceptable salt thereof in a pharmaceutically acceptable solvent, said solution having a nicotine concentration of 1 mg/ml to less than 9 mg/ml.

2. A method in ocordance with claim 1, wherein the nicotine concentration of said solution is in the range of about 1 mg/ml to 8 mg/ml.

3. A method in accordance with claim 1, wherein the nicotine concentration of said solution is in the range of about 5 mg/ml to less than 9 mg/ml.

4. A method in accordance with claim 1, wherein the nicotine concentration of said solution is in the range of about 4 mg/ml to less than 8 mg/ml.

5. A method in accordance with claim 1, wherein the pH of said solution is in the range of about 5.0 to 8.0.

6. A method in accordance with claim 5, wherein the pH of said solution is in the range of about 6.0 to 7.5.

7. A method in accordance with claim 6, wherein the pH of said solution is about 7.0.

8. A method in accordance with claim 1, wherein said droplets are about 10 to 200 microns in diameter.

9. A method in accordance with claim 1, wherein said droplets are about 10 to 100 microns in diameter.

10. A method in accordance with claim 1 wherein nasal symptoms associated with the administration of nicotine to the nasal mucosa of a subject are reduced compared to the nasal symptoms resulting from the administration of nicotine to the nasal mucosa in a concentration of 10 mg/ml or higher.

11. A method for reducing nasal symptoms associated with the administration of nicotine to the nasal mucosa of a subject and that enables a subject to stop smoking an decreases the desire of a subject to smoke, said method comprising administering to the subject one source of an effective amount of nicotine, said source being n the form of a nicotine nasal spray composition that can be administered to the nasal mucosa of the subject, the composition comprising droplets of about 10 to 200 microns in diameter, and a solution of nicotine or a pharmaceutically acceptable salt thereof in a pharmaceutically acceptable solvent, said solution having a nicotine concentration of about 5 mg/ml to less than 9 mg/ml and a pH of about 6.5 to 7.

12. A method in accordance with claim 11, wherein the nicotine concentration of said solution is in the range of about 4 mg/ml to 8 mg/ml.

13. A method in accordance with claim 1 that decreases the desire of a subject to smoke.

14. A method in accordance with claim 2 that enables the subject to stop smoking.

* * * * *

UNITED STATES PATENT AND TRADEMARK OFFICE
CERTIFICATE OF CORRECTION

PATENT NO. : 6,596,740 B2
DATED : July 22, 2003
INVENTOR(S) : Richard L. Jones

It is certified that error appears in the above-identified patent and that said Letters Patent is hereby corrected as shown below:

Title page,
Item [56], References Cited, OTHER PUBLICATIONS, "J. A. Stapleton et. al.," reference, insert -- J -- after "Brit Med";

Column 1,
Line 26, remove "(" before "concentration";
Line 67, replace "lose" with -- nose --;

Column 2,
Line 9, replace "Flerkins" with -- Perkins --;
Line 14, replace "requited" with -- required --;
Line 25, insert -- alone -- after "nicotine nasal spray";
Line 47, replace "s lt" with -- salt --;
Lines 50-51, remove "a out mg/ml, more preferably form";

Column 3,
Line 1, replace "mg/m" with -- mg/ml --;
Line 30, replace "tie" with -- the --;
Line 32, replace "uses" with -- used --;
Line 52, add -- . -- after "result";

Column 4,
Line 16, replace "lease" with -- least --;
Line 22, add -- . -- after "hydrogen tartrate";
Line 52, replace "strays" with -- sprays --;

Column 5,
Line 45, add -- . -- after "acid";
Line 57, add -- . -- after "deposition";

Column 6,
Line 7, replace "bloods" with -- blood --;
Line 41, add -- . -- after "concentration";
Line 44, remove "." after "ml";
Line 60, replace "with concentration is of nicotine of 10 mg/ml or greater involves administering" with -- with concentrations of nicotine of 10 mg/ml or greater which invlolves administering --;

Column 7,
Line 3, remove "," after "subject to";
Line 6, replace "once" with -- one --;

UNITED STATES PATENT AND TRADEMARK OFFICE
CERTIFICATE OF CORRECTION

PATENT NO. : 6,596,740 B2
DATED : July 22, 2003
INVENTOR(S) : Richard L. Jones

It is certified that error appears in the above-identified patent and that said Letters Patent is hereby corrected as shown below:

Column 7 (cont'd),
Line 19, replace "is" with -- as --;

Column 8,
Line 13, add -- . -- after "time";
Line 26, remove "." after "C";
Line 28, replace "bee" with -- by --;
Line 56, replace "differed ice" with -- difference --;

Column 9,
Line 52, add -- and -- after "solutions";

Column 10,
Line 8, add -- . -- after "frequently";
Line 58, remove ":" after "R.L.";

Column 11,
Line 31, replace "Tabasco" with -- tobacco --;
Line 52, replace "297" with -- 295 --;

Column 12,
Line 18, replace "ocordance" with -- accordance --;
Line 47, replace "an" with -- and --;
Line 50, replace "n" with -- in --.

Signed and Sealed this

Twenty-eighth Day of June, 2005

JON W. DUDAS
*Director of the United States Patent and Trademark Office*